US009675766B2

(12) United States Patent
Goldberg et al.

(10) Patent No.: US 9,675,766 B2
(45) Date of Patent: Jun. 13, 2017

(54) METHOD FOR PAIN-REDUCING SKIN PUNCTURE

(75) Inventors: Steven Goldberg, Boca Raton, FL (US); Michael Goldberg, Boca Raton, FL (US); David Schiff, Highland Park, NJ (US)

(73) Assignee: BING INNOVATIONS, LLC, Boca Raton, FL (US)

( * ) Notice: Subject to any disclaimer, the term of this patent is extended or adjusted under 35 U.S.C. 154(b) by 460 days.

(21) Appl. No.: 14/343,085

(22) PCT Filed: Sep. 5, 2012

(86) PCT No.: PCT/US2012/053744
§ 371 (c)(1),
(2), (4) Date: Aug. 25, 2014

(87) PCT Pub. No.: WO2013/036507
PCT Pub. Date: Mar. 14, 2013

(65) Prior Publication Data
US 2014/0371542 A1 Dec. 18, 2014

Related U.S. Application Data

(63) Continuation of application No. 13/253,572, filed on Oct. 5, 2011, now Pat. No. 9,168,340, and a
(Continued)

(51) Int. Cl.
*A61B 1/06* (2006.01)
*A61M 5/42* (2006.01)
(Continued)

(52) U.S. Cl.
CPC .............. *A61M 5/422* (2013.01); *A61B 90/30* (2016.02); *A61M 5/50* (2013.01); *A61M 37/0092* (2013.01); *A61M 2205/587* (2013.01)

(58) Field of Classification Search
CPC .. A61M 5/50; A61M 5/422; A61M 2005/587; A61M 37/0092
(Continued)

(56) References Cited

U.S. PATENT DOCUMENTS 1,485,963 A    3/1924  Curry
2,247,258 A    6/1941  Shepard
(Continued)

FOREIGN PATENT DOCUMENTS

AU    2010229783    9/2015
CA       2580792    10/2013
(Continued)

OTHER PUBLICATIONS

International Search Report, Written Opinion dated Nov. 30, 2012 for PCT/US12/53744.
(Continued)

*Primary Examiner* — Edelmira Bosques
(74) *Attorney, Agent, or Firm* — Paul D. Bianco; Fleit Gibbons Gutman Bongini & Bianco PL

(57) ABSTRACT

An instrument, article and method are provided for minimizing pain during administration by injection of a liquid, such as, an anesthetic. The instrument has a forward end. A rod or lightpipe mounted freely for vibration projects out of the forward end. The article, a single use tip, is composed of a tip sleeve removably mounted on the forward end of the instrument and a tip member removably mounted on the projecting rod or lightpipe to vibrate a preselected injection site on a human or animal. The tip sleeve and tip member are covered by an elastic overmold that enables the tip member to vibrate freely with respect to the tip sleeve and light from the lightpipe to illuminate the injection site. The overmold of the single use tip is torn during removal of the single use tip from the instrument.

11 Claims, 11 Drawing Sheets

Related U.S. Application Data continuation of application No. 13/225,782, filed on Sep. 6, 2011, now Pat. No. 8,622,952, said application No. 13/253,572 is a continuation-in-part of application No. 13/225,782, which is a continuation-in-part of application No. PCT/US2010/028858, filed on Mar. 26, 2010, and a continuation-in-part of application No. PCT/US2009/066033, filed on Nov. 29, 2009.

(60) Provisional application No. 61/163,945, filed on Mar. 27, 2009.

(51) Int. Cl.
    *A61M 5/50*     (2006.01)
    *A61M 37/00*     (2006.01)
    *A61B 90/30*     (2016.01)

(58) Field of Classification Search
USPC .................................. 604/113; 433/115–118
See application file for complete search history.

(56) References Cited

U.S. PATENT DOCUMENTS

| | | | |
|---|---|---|---|
| 2,258,857 A | 10/1941 | McCann | |
| 3,590,232 A | 6/1971 | Sadowski | |
| 3,620,209 A | 11/1971 | Kravitz | |
| 3,837,595 A | 9/1974 | Boone | |
| 4,091,805 A | 5/1978 | Clark | |
| 4,572,180 A | 2/1986 | Deenadayalu | |
| 4,593,973 A | 6/1986 | Yoshida | |
| 4,785,796 A | 11/1988 | Mattson | |
| 4,867,141 A | 9/1989 | Nakada et al. | |
| 5,437,606 A | 8/1995 | Tsukamoto | |
| 5,542,845 A | 8/1996 | Jenkins | |
| 5,636,988 A | 6/1997 | Murayama | |
| 5,639,238 A | 6/1997 | Fishburne, Jr. | |
| 5,647,851 A | 7/1997 | Pokras | |
| 5,647,853 A | 7/1997 | Feldmann et al. | |
| 5,692,900 A | 12/1997 | Fischer | |
| 5,704,902 A | 1/1998 | Vandenbelt et al. | |
| 5,928,170 A | 7/1999 | Garrigan | |
| 5,938,435 A | 8/1999 | Raspino | |
| 5,989,022 A | 11/1999 | Yamamoto | |
| 6,030,210 A | 2/2000 | Bianchetti | |
| 6,355,007 B1 | 3/2002 | Zuckerbrod | |
| 6,436,035 B1 | 8/2002 | Toth et al. | |
| 6,602,229 B2 | 8/2003 | Coss | |
| 6,923,762 B1 | 8/2005 | Creaghan, Jr. | |
| 7,244,266 B2 | 7/2007 | Garthe | |
| 7,981,071 B2 | 7/2011 | Goldberg | |
| 8,121,696 B2 | 2/2012 | Vallero | |
| 8,622,952 B2 | 1/2014 | Goldberg | |
| 8,668,664 B2 | 3/2014 | Goldberg | |
| 8,690,872 B2 | 4/2014 | Jayaraj | |
| 9,168,340 B2 | 10/2015 | Goldberg et al. | |
| 2002/0082564 A1 | 6/2002 | Pham | |
| 2003/0040714 A1 | 2/2003 | Coss | |
| 2003/0195644 A1 | 10/2003 | Borders et al. | |
| 2003/0225429 A1 | 12/2003 | Garthe et al. | |
| 2004/0077977 A1 | 4/2004 | Ella | |
| 2004/0254599 A1 | 12/2004 | Lipoma et al. | |
| 2005/0215952 A1* | 9/2005 | Brunel ................. | A61M 5/288 604/111 |
| 2006/0106363 A1 | 5/2006 | Aravena et al. | |
| 2007/0088245 A1 | 4/2007 | Babaev et al. | |
| 2007/0145155 A1 | 6/2007 | Scarlatella | |
| 2007/0156179 A1 | 7/2007 | S.E. | |
| 2007/0167943 A1 | 7/2007 | Janssen et al. | |
| 2008/0086159 A1 | 4/2008 | Zweifler | |
| 2008/0255483 A1 | 10/2008 | Goldberg | |
| 2009/0047624 A1 | 2/2009 | Tsai | |
| 2009/0281464 A1 | 11/2009 | Cioanta et al. | |
| 2010/0125172 A1 | 5/2010 | Jayaraj | |
| 2010/0179457 A1 | 7/2010 | Blaine | |
| 2011/0054386 A1 | 3/2011 | Blaine et al. | |
| 2011/0270154 A1 | 11/2011 | Goldberg | |
| 2011/0319812 A1 | 12/2011 | Goldberg et al. | |
| 2012/0016292 A1 | 1/2012 | Goldberg et al. | |
| 2012/0029422 A1 | 2/2012 | Goldberg | |
| 2013/0095508 A1 | 4/2013 | Campitelli et al. | |
| 2013/0197317 A1 | 8/2013 | Daniel et al. | |
| 2013/0204202 A1 | 8/2013 | Trombly et al. | |
| 2013/0317314 A1 | 11/2013 | Lampson | |
| 2014/0055588 A1 | 2/2014 | Bangera et al. | |
| 2014/0121557 A1 | 5/2014 | Gannon | |
| 2014/0187870 A1 | 7/2014 | Weber | |
| 2014/0188095 A1 | 7/2014 | Weber | |
| 2014/0188128 A1 | 7/2014 | Weber | |
| 2014/0343432 A1 | 11/2014 | Humayun | |
| 2014/0371542 A1 | 12/2014 | Goldberg | |
| 2014/0378940 A1 | 12/2014 | Lee | |
| 2015/0121557 A1 | 4/2015 | Pierce | |
| 2015/0134358 A1 | 5/2015 | Fisher | |
| 2015/0186702 A1 | 7/2015 | Pletcher et al. | |
| 2015/0216618 A1 | 8/2015 | Jayaraj | |
| 2015/0306286 A1 | 10/2015 | Ross et al. | |

FOREIGN PATENT DOCUMENTS

| | | |
|---|---|---|
| CN | 103826686 | 5/2014 |
| CN | ZL201080016524.X | 8/2014 |
| IL | 215355 | 9/2015 |
| JP | S6154832 | 4/1986 |
| JP | 548916 | 6/1993 |
| JP | 2002224183 | 8/2002 |
| JP | 2004129914 | 4/2004 |
| JP | 5549987 | 5/2014 |
| RU | 2011141339 | 5/2013 |
| RU | 2523203 | 5/2014 |
| WO | 03024513 A1 | 3/2003 |
| WO | 2004000196 A1 | 12/2003 |
| WO | 2006/034324 | 3/2006 |
| WO | 2008/042936 | 4/2008 |
| WO | 2010/110823 | 9/2010 |
| WO | 2010/111611 | 9/2010 |
| WO | 2013-036625 | 3/2013 |
| WO | 2015/081181 | 6/2015 |

OTHER PUBLICATIONS

International Preliminary Report on Patentability published Mar. 12, 2014 for PCT/US2012/053744.
Columbian Request for Technical Information dated Apr. 12, 2013.
Response to Columbian Request for Technical Information dated Jul. 15, 2013.
English translation of Japanese Office Action dated Jan. 7, 2014 for Japanese Patent Application No. JP2012-502291 filed on Sep. 20, 2012.
European Search Report (ESR) for EP application No. 107569266. 1—PCT/US2010028858 dated Aug. 20, 2013.
For U.S. Appl. No. 13/253,572 Office Actions dated Sep. 17, 2013; Feb. 6, 2014 Responses filed Dec. 17, 2103; May 5, 2014.
Response to Japanese Office Action dated Mar. 24, 2014 for Application No. JP2012521809 filed Sep. 20, 2012.
Office Action Summary dated Dec. 18, 2013 for MX/a/2011/010069.
International Search Report dated Dec. 13, 2012 for International Patent Application No. PCT/ US2012/053943 filed Sep. 6, 2012.
International Preliminary Report of Patentability (IPRP) published Mar. 12, 2014 and Written Opinion (WO) published Mar. 6, 2014 for International Patent Application No. PCT/ US2012/053943 filed Sep. 6, 2012.
Russian Decision on Granting a Patent for Invention filed on Mar. 26, 2010 for Patent Application No. RU2011141339 filed May 10, 2013.
Office action dated Jan. 23, 2013 for Israeli application No. 215355.
Response to office action dated Jul. 2013 for Israeli application No. 215355.

(56) References Cited

OTHER PUBLICATIONS

Response to Mexican Office Action dated Feb. 4, 2014 for Mexican Application No. MX/a/2011/010069, with English translation.
Office Action dated Mar. 31, 2014 for MX/a/2011/010069.
First Office Action for Chinese Application No. 201080016524X with English translation from Chinese associate dated Nov. 20, 2012.
Response to First Chinese Office Action for Application No. 201080016524X dated Jun. 5, 2013.
Second Office Action for Chinese Application No. 201080016524X with English translation from Chinese associate dated Jul. 25, 2013.
Response to Second Chinese Office Action for Application No. 201080016524X dated Dec. 5, 2013.
Third Office Action for Chinese Application No. 201080016524X with English summary from Chinese associate dated Feb. 27, 2014.
Australian Patent Examination Report No. 1, dated May 5, 2014 for Patent application No. 2010229783, based on PCT/US10/028858.
Response to the notice prior to examination for Israeli application No. 215355 filed May 12, 2014.
Notice Prior of Allowance dated Jul. 16, 2014 for Israeli application No. 215355.
Ronald Melzack and Patrick Wall. What is Gate Control Theory?, about.com Psychology, 1960.
Jul. 21, 2013 response to Jan. 23, 2013 Office Action for Israel Application No. 215355.
Response dated Mar. 12, 2014 to Office Action dated Sep. 6, 2013 for EP Application 10756926.1.
Response dated May 12, 2014 to third Office Action for Chinese Patent Application No. 201080016524.X.
Supplemental Response filed Oct. 10, 2013 for U.S. Appl. No. 13/179,674.
Office Action for U.S. Appl. No. 13/253,572 dated Sep. 17, 2013.
Notice of Allowance dated Oct. 21, 2013 for U.S. Appl. No. 13/179,674.
Notice of Publication for China application No. 201280043253.6 dated Jun. 5, 2014.
Supplementary European Search Report dated May 18, 2010 for Application No. EP05803150.
International Search Report published on Nov. 2, 2006, for PCT/US2005/33769, filed Sep. 19, 2005.
International Preliminary Report on Patentability published Mar. 20, 2007, for PCT/US2005/33769, filed Sep. 19, 2005.
Written Opinion published on Mar. 20, 2007, for PCT/US2005/33769, filed Sep. 19, 2005.
International Search Report dated Apr. 10, 2008, for PCT/US2007/80262, filed Oct. 3, 2007.
Written Opinion dated Apr. 10, 2008, for PCT/US2007/80262, filed Oct. 3, 2007.
International Preliminary Report on Patentability dated Apr. 7, 2009, for PCT/US2007/80262, filed Oct. 3, 2007.
International Search Report dated Jul. 16, 2010 for PCT/US2009/066033, published Sep. 30, 2010.
Written Opinion dated Jul. 15, 2010 for PCT/US2009/066033, published Sep. 30, 2010.
International Preliminary Report on Patentability dated Sep. 27, 2011 for PCT/US2009/066033, published Sep. 30, 2010.
International Search Report dated Dec. 21, 2010 for PCT/US10/28858 filed Mar. 26, 2010.
Written Opinion dated Dec. 20, 2010 for PCT/US10/28858 filed Mar. 26, 2010.
International Preliminary Report on Patentability dated Sep. 27, 2011 for PCT/US10/28858 filed Mar. 26, 2010.
Russian Decision on Granting for Russian application No. 2011141339/02 (061869) dated Mar. 19, 2014.
Japanese Office Action dated Jan. 7, 2014 for JP 2012-502291.
Decision to Grant for JP 2012-502291 dated Apr. 17, 2014.
Office Action dated Oct. 16, 2014 for U.S. Appl. No. 13/259,408.

Response Office Action filed Oct. 22, 2014 for Israeli Application No. 215355.
Notice of Allowance dated Oct. 2, 2014 for European Application No. 05 803 150.1-1651.
Notice of Allowance dated Oct. 6, 2014 for Mexican Application No. MX/A/2011/010069.
Notice of Allowance dated Oct. 21, 2013 for U.S. Appl. No. 13/179,674, filed Jul. 11, 2011.
Official action from European Patent Office for EP 05 803 150.1-1651 dated Nov. 16, 2011.
Response to official action from European Patent Office for EP 05 803 150.1 dated Mar. 26, 2012.
Second official action from European Patent Office for EP 05 803 150.1 dated Feb. 20, 2014.
Response filed with European Patent Office confirming applicant wishes to proceed for EP 05 803 150.1 dated Dec. 20, 2010.
Response to Mexican office action dated Jun. 9, 2014 for Mexican Patent Application No. MX/A/2011/010069.
Notice of Allowance for U.S. Appl. No. 13/253,572 dated Sep. 18, 2014.
Notice of Publication for HK Application No. 14108064.8 dated Sep. 26, 2014.
For U.S. Appl. No. 13/179,674; office action dated Oct. 16, 2012; response dated Jan. 16, 2013; final office action dated Mar. 18, 2013; response dated Aug. 19, 2013.
For U.S. Appl. No. 13/225,782: notice of allowance dated Sep. 5, 2013.
Notice Prior to Allowance dated Dec. 31, 2014 for Israeli Patent Application No. 215355.
Supplementary European Search Report dated Jan. 7, 2015 for European Application No. 12829549.
European Communication dated Jan. 23, 2015 for European Application No. 12829549.
Notice of Allowance dated Feb. 13, 2015 for U.S. Appl. No. 13/253,572.
International Search Report and Written Opinion of the International Searching Authority mailed Feb. 25, 2015 for PCT/US2014/67587.
Office Action dated Jul. 12, 2016 for U.S. Appl. No. 14/343,085.
Response to Final Office Action, dated Jul. 18, 2016 for U.S. Appl. No. 13/259,408.
Final Office Action dated Apr. 16, 2015 for U.S. Appl. No. 13/259,408.
Response filed May 21, 2015 to Final Office Action dated Apr. 16, 2015 for U.S. Appl. No. 13/259,408.
Taiwanese Office Action dated May 15, 2015 for Application No. 101132425.
International Search Report and Written Opinion for PCT/US16/29938 dated Aug. 25, 2016.
Office Action dated Jul. 20, 2016 for Japanese Patent Application No. JP2014-528700.
Response filed Oct. 26, 2015 to Office Action dated Jun. 25, 2015 for U.S. Appl. No. 13/259,408.
Office Action dated Dec. 14, 2015 for U.S. Appl. No. 14/803,535.
Final Office Action dated Jan. 20, 2016 for U.S. Appl. No. 13/259,408.
Response filed Feb. 12, 2016 to Office Action dated Dec. 14, 2015 for U.S. Appl. No. 14/803,535.
Office Action dated Apr. 8, 2016 for Korean Patent Application No. 10-2011-7025440.
Response filed Jun. 8, 2016 for Office Action dated Apr. 8, 2016 for Korean Patent Application No. 10-2011-7025440.
Notice of Allowance dated Jun. 7, 2016 for U.S. Appl. No. 14/803,535.
International Preliminary Report on Patentability dated May 31, 2016 for PCT/US2014/067587.
Office Action dated Jun. 25, 2015 for U.S. Appl. No. 13/259,408.
Office Action dated Jun. 4, 2015 for Chinese Application No. 2012800432536.

* cited by examiner

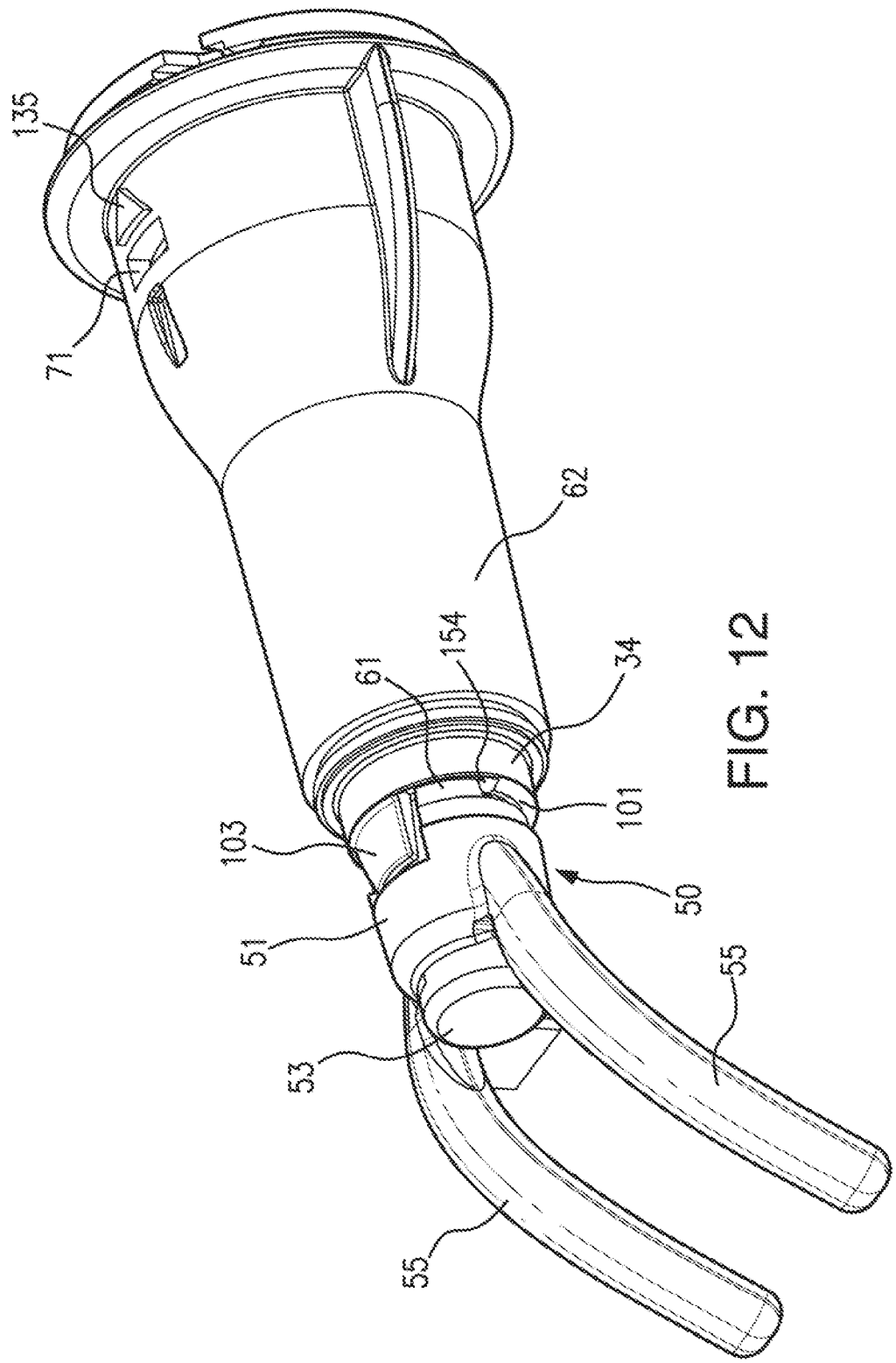

METHOD FOR PAIN-REDUCING SKIN PUNCTURE

CROSS REFERENCE TO RELATED APPLICATIONS

This application and the invention described herein claim the benefit of priority to U.S. patent application Ser. No. 13/253,572 filed Oct. 5, 2011 and U.S. patent application Ser. No. 13/225,782 filed Sep. 6, 2011. U.S. patent application Ser. No. 13/253,572 is a continuation-in-part of U.S. patent application Ser. No. 13/225,782, which is a continuation-part of PCT Application No. PCT/US2010/028858 filed Mar. 26, 2010, which is a continuation-in-part of PCT Application No. PCT/US2009/066033 filed Nov. 29, 2009, which claimed priority to U.S. Provisional Patent Application No. 61/163,945 filed Mar. 27, 2009. This application and the invention described herein also relate to co-owned U.S. Pat. No. 7,981,071 issued Jul. 19, 2011, which was a U.S. National Stage Application of PCT Application No. PCT/US2005/033769 filed Sep. 19, 2005, which claimed priority to U.S. Provisional Patent Application No. 60/707,754 filed Aug. 12, 2005 and U.S. Provisional Patent Application No. 60/611,497 filed Sep. 20, 2004. Each of the above-identified applications is herein incorporated by reference in their entirety.

FIELD OF INVENTION

The invention relates to improvements to a method, article and apparatus for use in medical and dental procedures, and particularly to improvements to a method and apparatus in the form of a retractor vibrator and the article in the form of a disposable tip for reducing or minimizing pain during tissue or skin puncturing procedures, such as, administration by injection, into the gums, skin or other tissue of a patient, of a liquid, such as, and in particular, an anesthetic.

BACKGROUND OF THE INVENTION

As described in former applications, in the prior art, the normal procedure for reducing the pain when injecting a liquid, such as, an anesthetic, serum, vitamins, vaccine, or other medical or dental efficacious liquids is either to (a) place a very cold material against the skin or flesh of the patient at the injection site, (b) to apply a topical treatment to the skin or flesh at the injection site, which temporarily numbs the skin or flesh or (c) rapidly manually massaging the skin or tissue at the injection site while performing the injection. Although these procedures have some effect, they are either cumbersome, require some time to complete or are of limited effect and do not reduce the pain to a satisfactory level. The invention described in the former applications provided a unique and novel apparatus and method for reducing pain during skin puncturing procedures, particularly involving dentistry.

SUMMARY OF THE INVENTION

It is a general object of the present invention to provide improvements to the inventions described in the former applications, especially regarding the retractor vibrator and single use or disposable tip described. Through the use of the improvements described and claimed herein further disadvantages will be overcome when injecting an anesthetic, serum, vitamins, vaccine, or other medical or dental efficacious liquids. In particular, it is an object of the present invention to provide improvements to the apparatus, article and method previously described that can be easily and inexpensively utilized during a medical, veterinary or dental procedure to almost completely or substantially eliminate the pain attendant an injection as it punctures the skin or flesh of the patient.

In keeping with the objects of the present invention, the present invention comprises an improved method, an improved article in the form of a disposable tip and an improved hand-held apparatus, in its preferred form of a retractor vibrator, for vibrating a skin or tissue area, and preferably at least two skin or tissue areas or a circular skin or tissue area, immediately at an injection site simultaneously with injection by needle of a liquid, such as, an anesthesia, serum, vitamins, vaccine, or other medical or dental efficacious liquids, into the skin or tissue at the injection site in a more effective and sanitary manner. The region of interest for a dentist is the entire oral mucosa area and underlying bone whereas the region of interest for a medical doctor is the whole body and underlying bone. Such a typical injection procedure may involve an injection of Lidocaine into a patient's gum or other tissue during a dental procedure.

Accordingly it is an object of the invention to provide an improved instrument for minimizing pain during administration by injection of a liquid, such as, an anesthetic comprising a main body, a single use detachable tip (novel article) cantilever mounted on the main body in a unique manner to prevent re-use of the tip and a vibration unit mounted in the main body when initiated to cause the tip to vibrate in a unique and novel manner. The tip is vibrated and has a free end characterized by a bifurcation to form two spaced projections defining a space between them, whereby the spaced projections can be placed in proximity to a preselected injection site on a human or animal and the tissue at said preselected injection site vibrated while an injection is given, and then continuing the vibration to massage the tissue to dissipate the injected liquid into the tissue and prevent tissue distension and swelling of the tissue. Preferably, the subsequent vibration is effected with more pressure on the tissue by the person injecting to effect better massaging. The subsequent vibration is most effective if the pressure applied is sufficient to sound bone beneath the tissue. An ordinarily skilled-in-the-art dentist can sense when he is applying pressure to tissue, such as the gums, and his instrument is touching the gums is in good contact or effectively hitting on underlying bone. When tissue or bone contact is sensed, the pressure is maintained for 1 to 90 seconds. The area of the injection site is lighted by the instrument in a unique way. Also, improved performance is obtained by pulsing the vibrations according to a preferred duty cycle, such about one second on and about $\frac{1}{10}^{th}$ of a second off.

As a further improvement, the article in the form of a single use or disposable tip is comprised of a tip sleeve composed of a hard plastic such as polycarbonate, for mounting on the forward portion of an instrument by means of a detachable connection, such as a bayonet type, and a forked tip member, also composed of a hard plastic, which parts are held together in a slightly spaced relation by an overmold of rubber or a thermoplastic elastomer having a preselected durometer. The forked tip member has a plastic cup formed in its base that is mounted on the vibrated lightpipe that projects out from the front of the instrument. A lens formed in the end of the cup shines light from the lightpipe onto the injection site. The prongs of the forked tip member extend forwardly and bend downwardly at an angle of approximately 55 degrees. An O-ring holds the lightpipe centered in the forward part of the instrument while allowing the lightpipe to vibrate freely.

As further objects of the invention an improved instrument as above can be arranged wherein the detachable tip includes a surface to act as a retractor, a control switch can be provided on the main body for on/off control of the vibration unit. Also, the tip can include an element that coacts with the improved instrument so that when placed on the improved instrument, the element activates a switch or contacts to turn the improved instrument on. When the tip is removed by the necessary manipulation, the overmold of rubber or a thermoplastic elastomer is torn drastically so that reuse of the tip is impossible. As in the previous instrument, the improved instrument can include a music player in the main body for playing music through a speaker. Further the main body can include rechargeable batteries as a power source to drive the vibration unit. Still further a light source is provided on the main body directed toward the space defined between the spaced projections to light the area being injected to provide better visibility.

Also, another object of the invention includes a method comprising the steps of vibrating tissue of a human or animal in a unique manner that maintains the vibration fresh and effective in proximity to a preselected injection site while simultaneously injecting by a needle or like instrument a liquid at the preselected injection site, and then continuing the vibration with more pressure applied to massage the injection site to dissipate the injected liquid and distribute it into the surrounding tissue.

The objects of the invention are accomplished by an instrument for minimizing pain during administration by injection of a liquid, such as, an anesthetic comprising a main body having a forward end, a light-transmitting rod or lightpipe mounted in said body freely for vibration and projecting out of said forward end, a tip composed of a tip sleeve removably mounted on the forward end of said main body and a pronged tip member having a forward bifurcation defining a preselected injection site on a human or animal removably mounted on the lightpipe. The tip sleeve and pronged tip member are covered and held together by an elastic overmold while allowing light from said light rod to illuminate the injection site, a vibration unit mounted in the main body and coupled to said light rod such that when initiated imparts vibrations via said light rod to said pronged tip member. The instrument can comprise means for controlling the vibration unit for an on-off duty cycle; the duty cycle can be about 1 second on and about $\frac{1}{10}$ second off. The pronged tip member may include at least one surface to act as a retractor. The tip sleeve and main body can include mutually coacting members to prevent reuse of said tip. A music player may be included in the main body for playing music through a speaker. The light rod is preferably composed of polycarbonate and the light rod is held by an O-ring at the forward end in order to be vibrated freely.

The objects of the invention are further accomplished by providing an instrument for minimizing pain during administration by injection of a liquid, such as, an anesthetic comprising a main body having a forward end, a light rod mounted in said body extending toward said forward end, a single use disposable tip composed of a tip sleeve removably mounted on the forward end of said main body and a pronged tip member having a forward bifurcation defining a space that brackets a preselected injection site on a human or animal removably mounted on the light rod, said tip sleeve and pronged tip member being covered and held together by an elastic overmold while allowing light from said light rod to illuminate the injection site, a vibration unit mounted in the main body and coupled to said light rod such that when initiated imparts vibrations to said pronged tip member via said light rod, said tip and main body having mutually coacting elements such that once the tip is placed on said main body, its removal automatically prevents reuse of said tip. The instrument can include means for controlling the vibration unit for an on-off duty cycle, which is preferably set for a duty cycle is about 1 second on and about $\frac{1}{10}$ second off. The pronged tip member can include at least one surface to act as a retractor.

The objects of the invention with respect to a method may comprise the steps of vibrating tissue of a human or animal in proximity to, adjacent to and bracketing a preselected injection site while simultaneously illuminating an injection site and injecting by a needle or like instrument a liquid at the preselected injection site, wherein the vibration is pulsed. The pulsing is preferably about 1 second on and about $\frac{1}{10}$ second off.

The objects of the invention with respect to an article comprise providing a single use disposable tip for use with an instrument that includes a vibration unit and a lightpipe (transparent or translucent rod that transmits light) that is vibrated by the vibration unit, the lightpipe projecting out of the forward end of the instrument, the tip comprising a tip sleeve for removably mounting on the forward end of instrument and a pronged tip member for removably mounting on the projecting lightpipe. The pronged tip member has a forward bifurcation defining a preselected injection site on a human or animal. The tip sleeve and pronged tip member are covered and held together by an elastic overmold that enables the pronged tip member to vibrate freely with respect to the tip sleeve and light from the lightpipe to illuminate the injection site. The single use disposable tip, i.e. the tip sleeve and the pronged tip member are spaced apart and an annular space between them is covered with overmold. The pronged tip member comprises a cup and an integrally formed pair of longitudinally extending prongs with the overmold of the prongs having a wider portion to provide at least one retraction surface and on the underside grooves to collect saliva to insure that the disposable tip is not reused. At least one longitudinal groove may be formed in the wider portion of the overmold. Also, the overmold at the ends of the prongs is preferably bulbous. The forward end of the tip sleeve preferably defines an alternate groove and rib and the overmold fills the groove and anchors in the rib.

BRIEF DESCRIPTION OF THE DRAWINGS

The above-mentioned features and objects of the present invention will be discussed in terms of the attached figures wherein like reference numerals denote like elements and in which:

FIG. 12 is an assembly view in perspective showing the tip mounted on the instrument sleeve.

DETAILED DESCRIPTION OF PREFERRED EMBODIMENTS OF THE INVENTION

Figure 1:
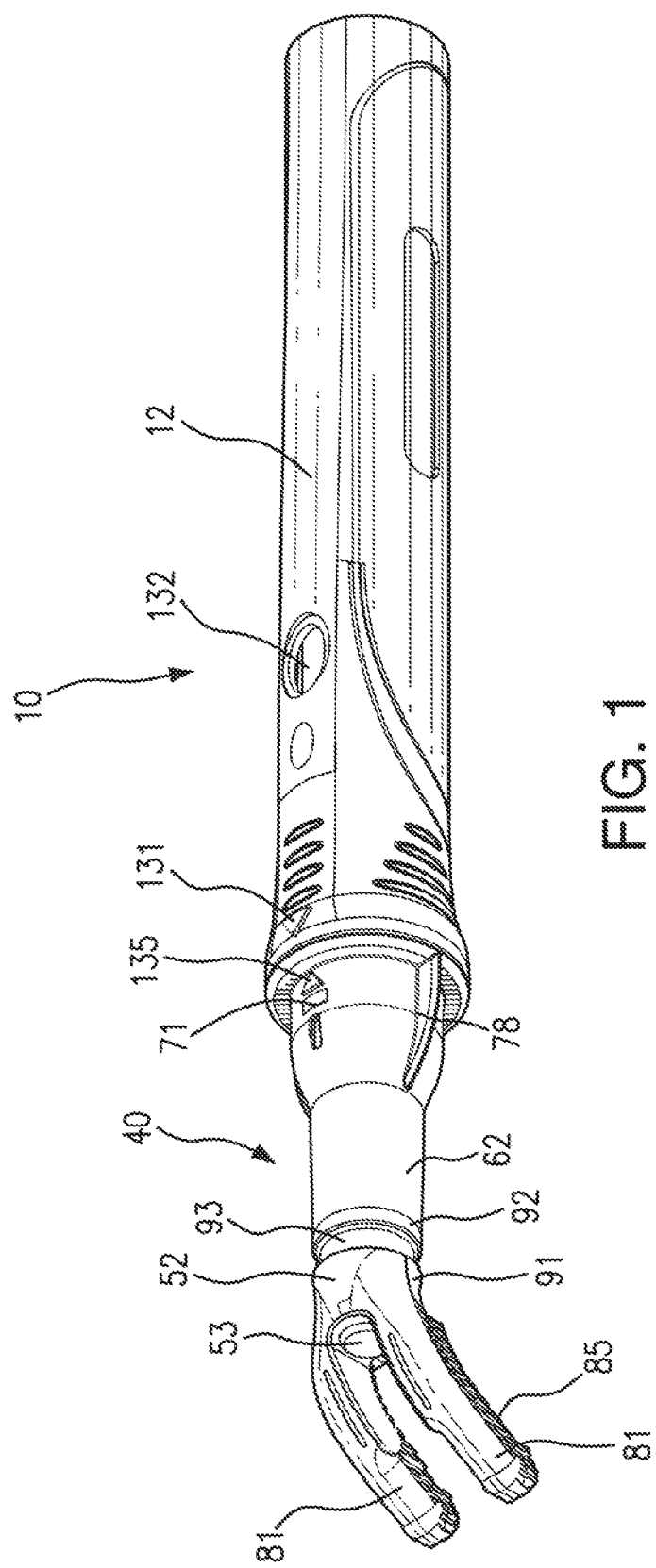
FIG. 1 is a perspective view of the novel instrument with a disposable tip mounted thereon.

Referring to FIGS. 1 to 12, an embodiment of the improved retractor vibrator is shown generally in FIG. 1 designated as 10 for performing the functions of the present invention, as will be explained hereinafter. Exploded views are shown in FIGS. 2-5. In particular, retractor vibrator 10 is a handheld apparatus comprising a main body or handle 12 in the shape of a tube having a battery cover and an end closure that is threaded to screw onto the open end of handle 12 in a complementary fit. This is as described in WO/2010/111611, hereby incorporated by reference in its entirety. Further as described in WO/2010/111611 handle 12 is composed of hard plastic and partially receives a chassis, the uncovered portion of which is covered by a battery cover. Rechargeable batteries, not shown in FIG. 1, are located in a battery compartment of the chassis. An induction coil is mounted on the end of chassis and positioned in the battery cover to couple to a charge device in a conventional manner. A motor 24 shown schematically in phantom in FIG. 7 drives eccentrically a cam 26 in phantom and is housed in the handle 12. Cam 26 includes a ball socket whose axis is offset from the motor drive axis by from about 0.010 inches to about 0.025 inches, with an offset of about 0.020 inches being preferred. The vibration induced by the cam 26 and follower 100 fixed to rod 30 via a fitting 31 at its rear end is transmitted via polycarbonate light rod 30 to polycarbonate tip 50 firmly engaged with rod 30 at its forward end, see FIG. 6 and the cross section of FIG. 7 in particular. The vibrations produced at the free ends of the two bifurcated legs 42 of tip 50 will have amplitude of about 0.5 mm (0.020 inches). During vibration, the light rod 30 is free from all other structure except the cam 26 at its rear end and tip 50 at its forward end so that it can vibrate freely by pivoting about resilient ring 29 (rubber or plastic O-ring) mounted in a groove 14 formed in rod 30 spaced from the forward end of rod 30. The rod 30 has projections 16 on the rear side of the groove 14 to assist in holding the O-ring 29 in correct position. The forward end of the rod 30 firmly engaged with tip 50. Also as in the structure described in WO/2010/111611, a PCB board containing electrical and electronic circuitry is mounted on the chassis (not shown). The battery (not shown) is connected via the circuitry to control the motor in the manner described in WO/2010/111611 here incorporated by reference. When the motor 24 is driven, vibration produced by the cam 26 is coupled to polycarbonate light rod 30 via a coupling fitting and cam follower 100. A light 36, preferably an LED, is positioned at the rear end of the rod 30 and powered by the battery and circuitry, as described in WO/2010/111611.

Figure 2:
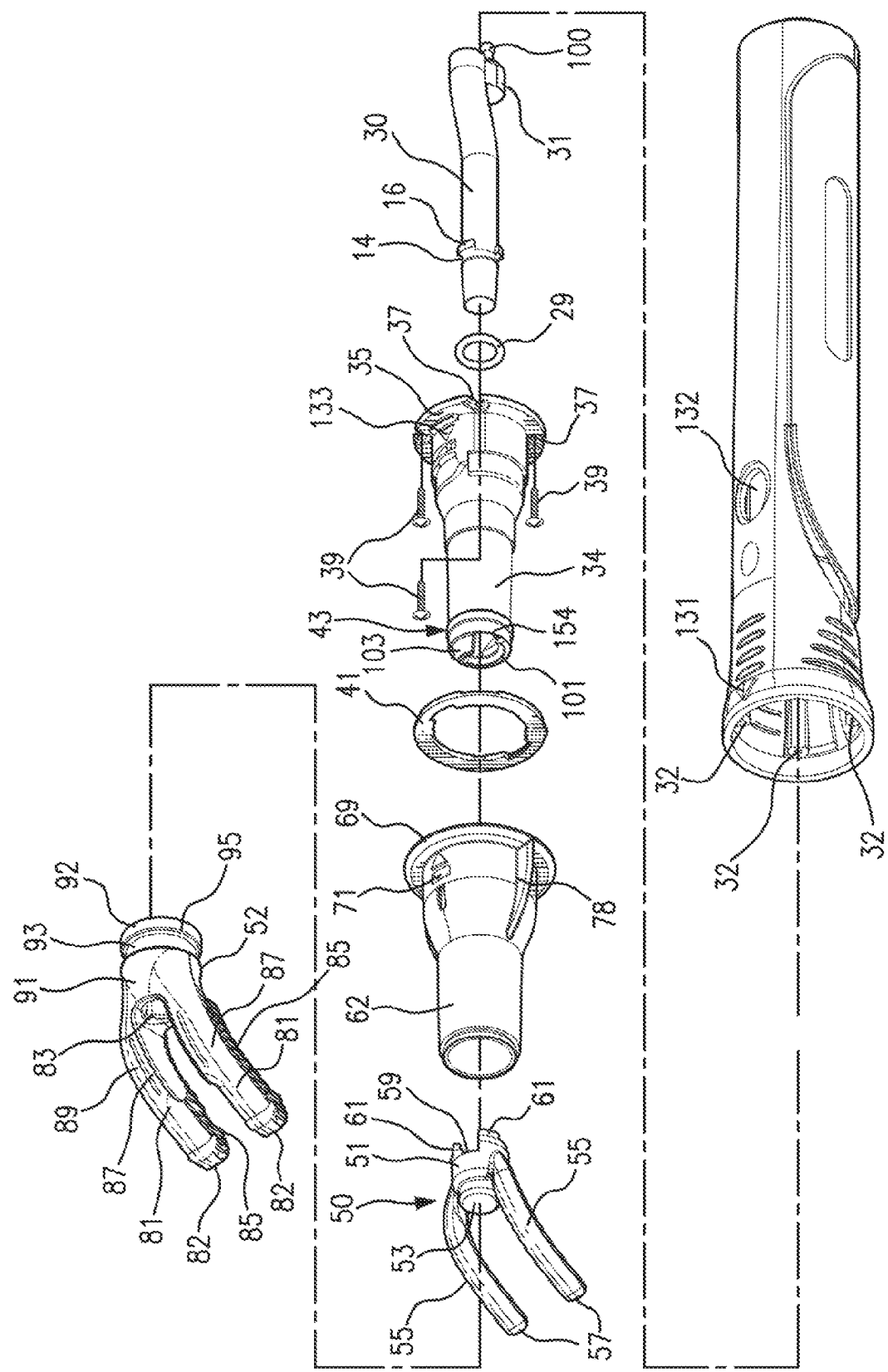
FIG. 2 is an exploded drawing showing an embodiment of the apparatus of the present invention with a disposable tip.
Figure 3:
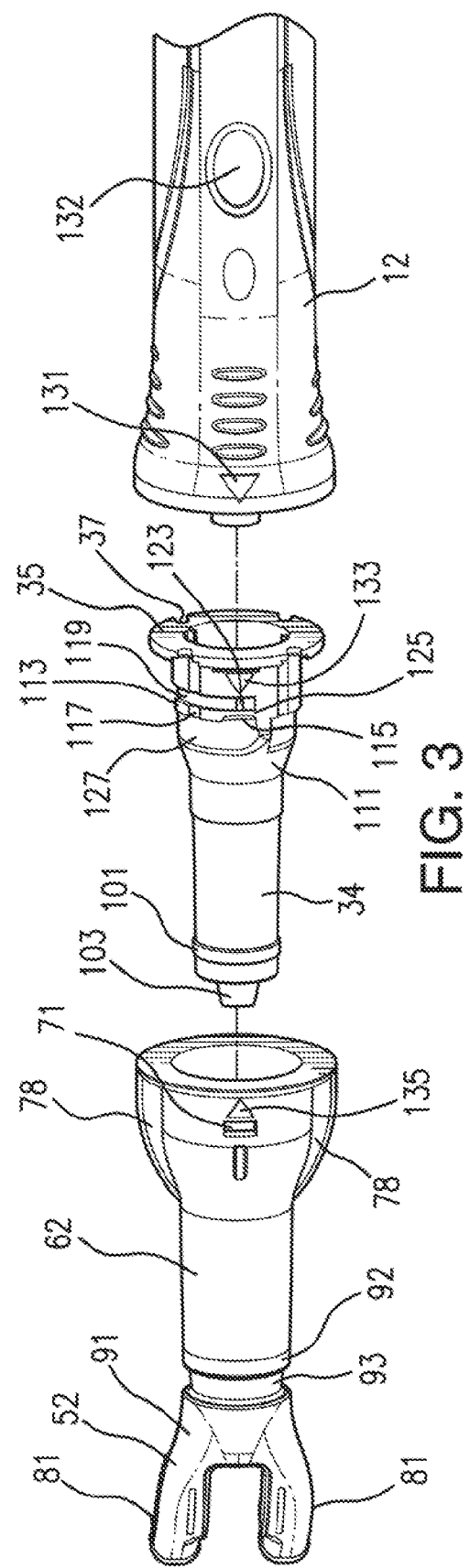
FIG. 3 shows in an exploded drawing how the removable or disposable tip is mounted on the end of the instrument.
Figure 4:
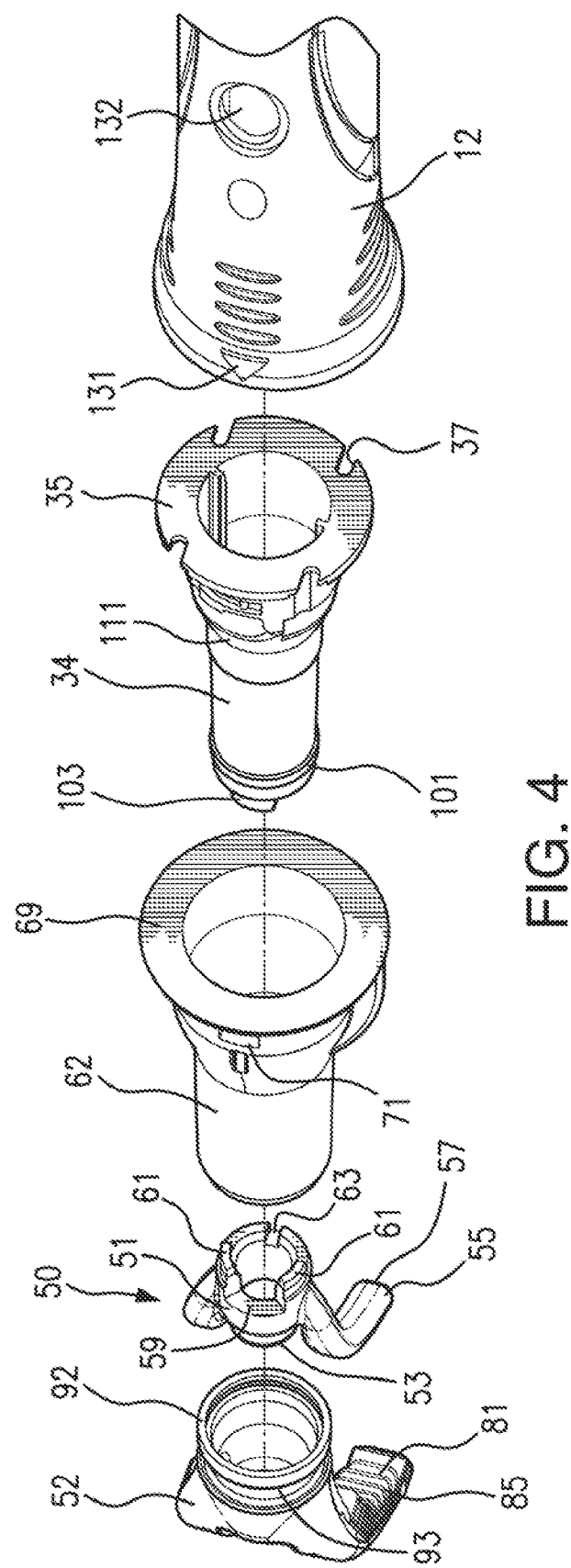
FIG. 4 shows in an exploded drawing in a different perspective the main components of the instrument.
Figure 5:
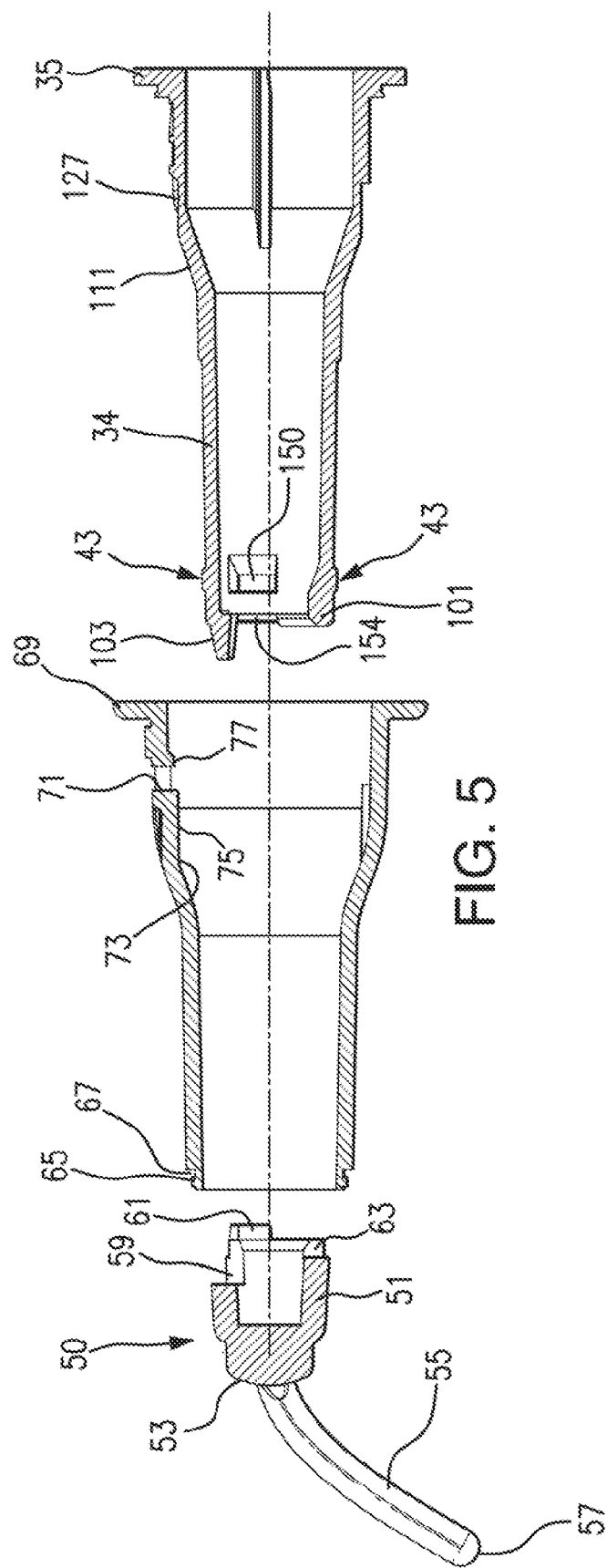
FIG. 5 shows in an exploded drawing in section the handle sleeve, the tip sleeve and the plastic tip of the instrument.
Figure 6:
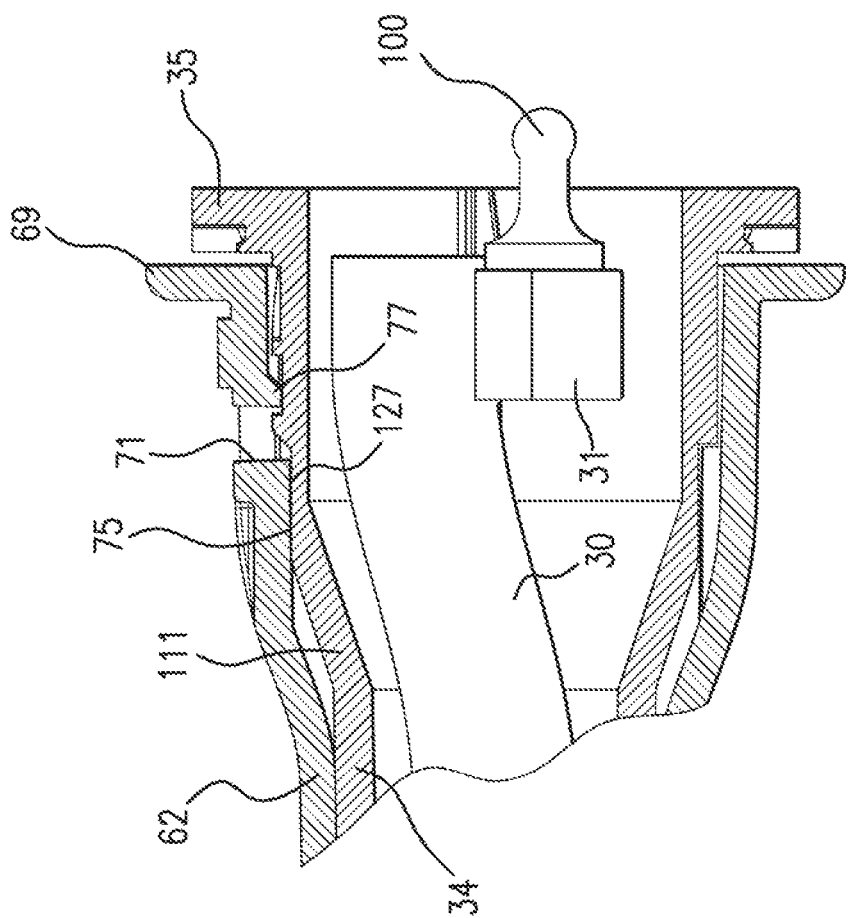
FIG. 6 shows in section the rear portion of the assembly view of FIG. 7 showing the position of the light rod of the instrument.

The forward end of the handle 12 is provided with 4 recessed bolt mountings 32, see FIG. 2. A handle sleeve 34 has a flange 35 at its rear end provided with 4 bolt openings 37 to receive bolts 39 to fix the handle sleeve 34 in a recessed position to the handle 12. A cover annulus 41 is fitted into the handle 12 to close the opening and cover the bolts 39. The light rod 30 passes through the handle sleeve 34 and projects outwardly from it. The O-ring 29 resiliently engages the inner surface of the handle sleeve 34 near its forward end. The front end of the handle sleeve 34 has a low flange 43 set back from the open front end.

Figure 10:
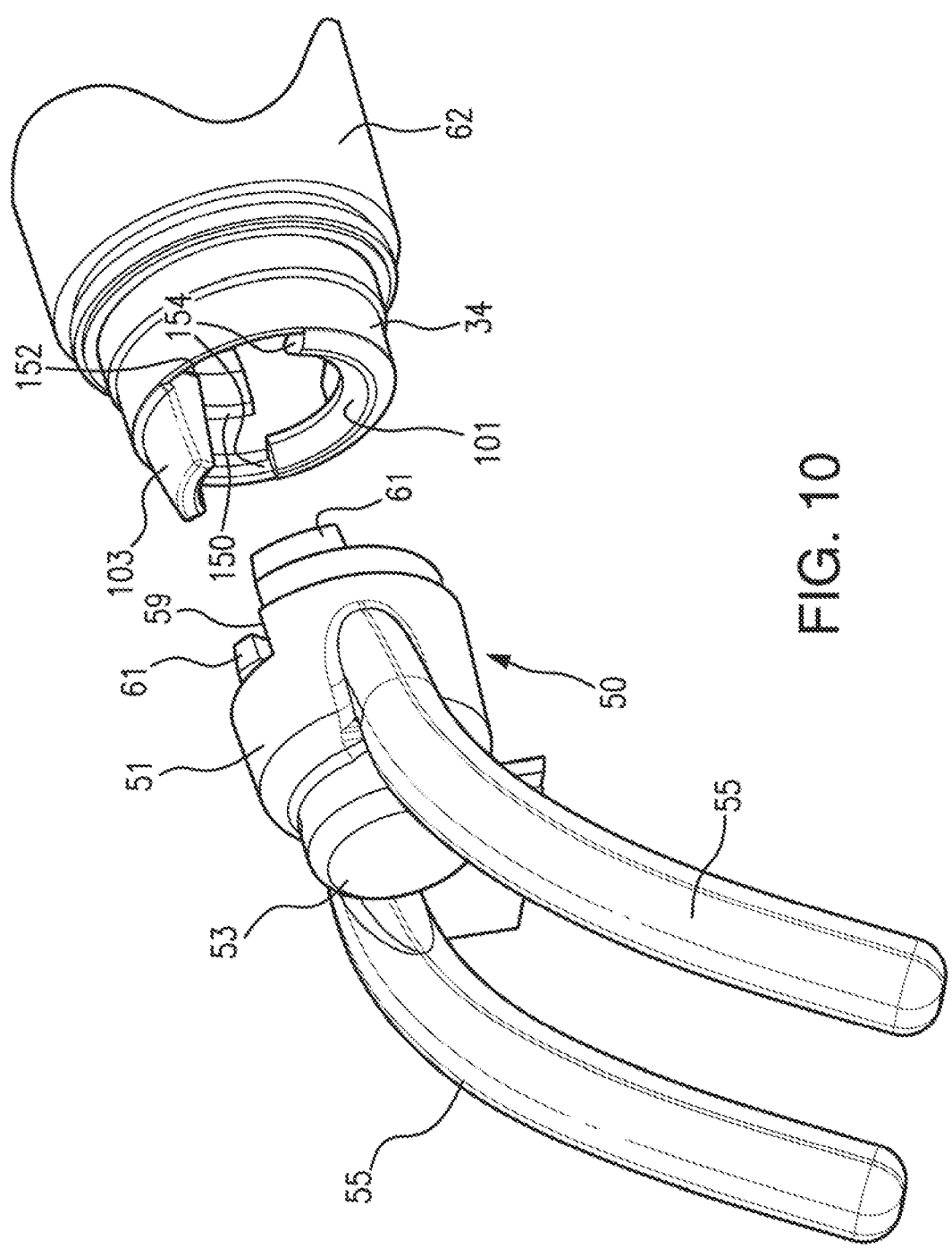
FIG. 10 is an exploded view in perspective showing the tip mounting to the instrument sleeve.
Figure 11:
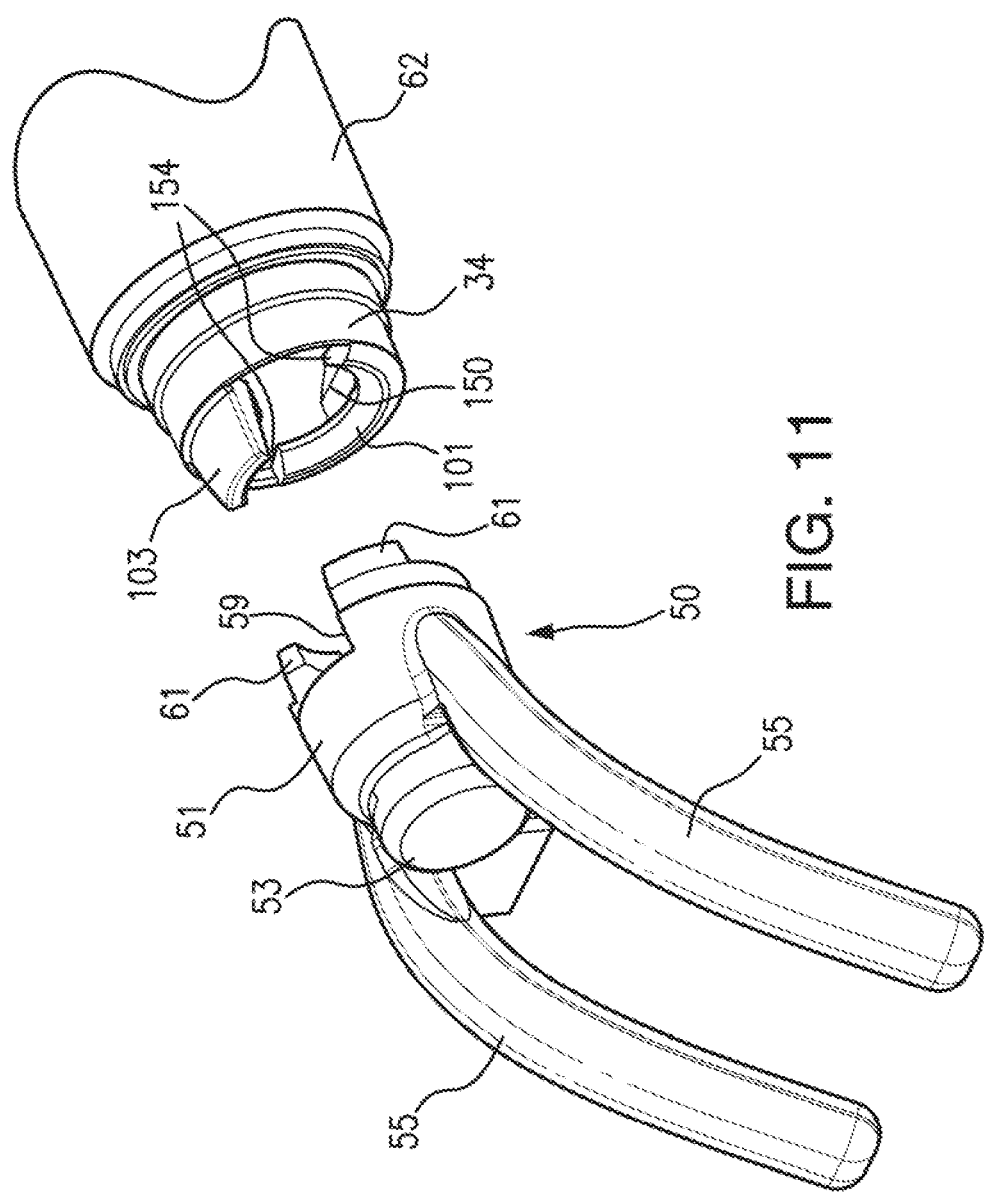
FIG. 11 is a similar exploded view in perspective showing the tip just before mounting on the instrument sleeve.

The handle sleeve 34 receives a single use disposable tip 40, See FIGS. 10-12, comprised of three components, namely, a forward plastic tip 50 that is firmly but detachably mounted on the end of light rod 30, a tip sleeve 62 for detachably and rigidly being mounted on handle sleeve 34 and a resilient (rubber or plastic) overmold 52 that covers the plastic tip 50 and holds tip 50 and tip sleeve 62 together in a spaced relationship that enables tip 50 to vibrate freely relative to tip sleeve 62.

Each component of the disposable tip 40 will now be described in more detail. The plastic tip 50 consists of a cup 51 with its closed end defining a lens 53. Two curved protrusions or legs 55 extend from the sides of the cup 51 bracketing the lens 53, extending forwardly and terminating in free ends 57 that are rounded. On its rear facing side, the cup 51 has a cutout 59 and two tongues, tabs or positive ribs 61 that extending rearward, one on each side of the cutout 59. Diametrically opposite cutout 59 is a small cutout 63. The rod 30 enters into the cup 51 and firmly and rigidly engages the cup 51 and the forward end of the rod 30 is juxtaposed closely to the lens 53.

Figure 8:
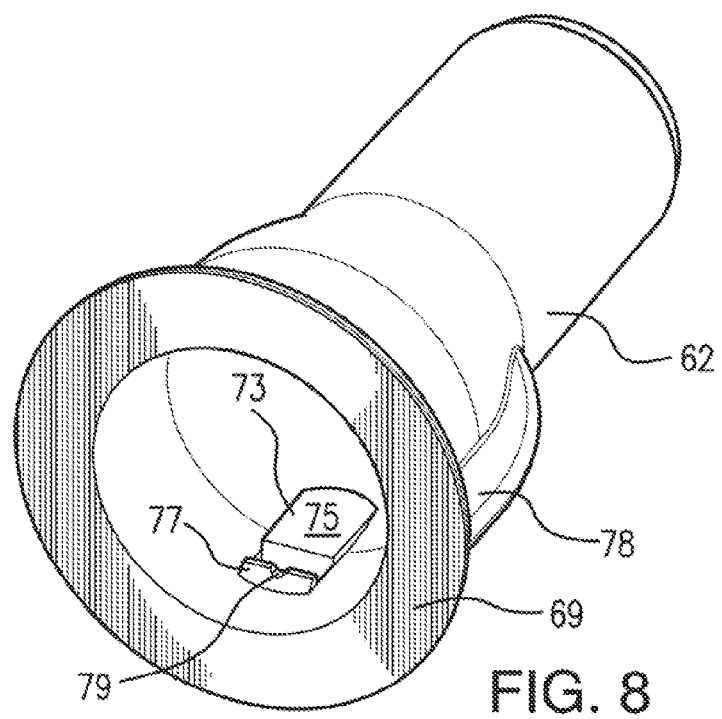
FIG. 8 is a perspective view showing the tip sleeve.
Figure 9:
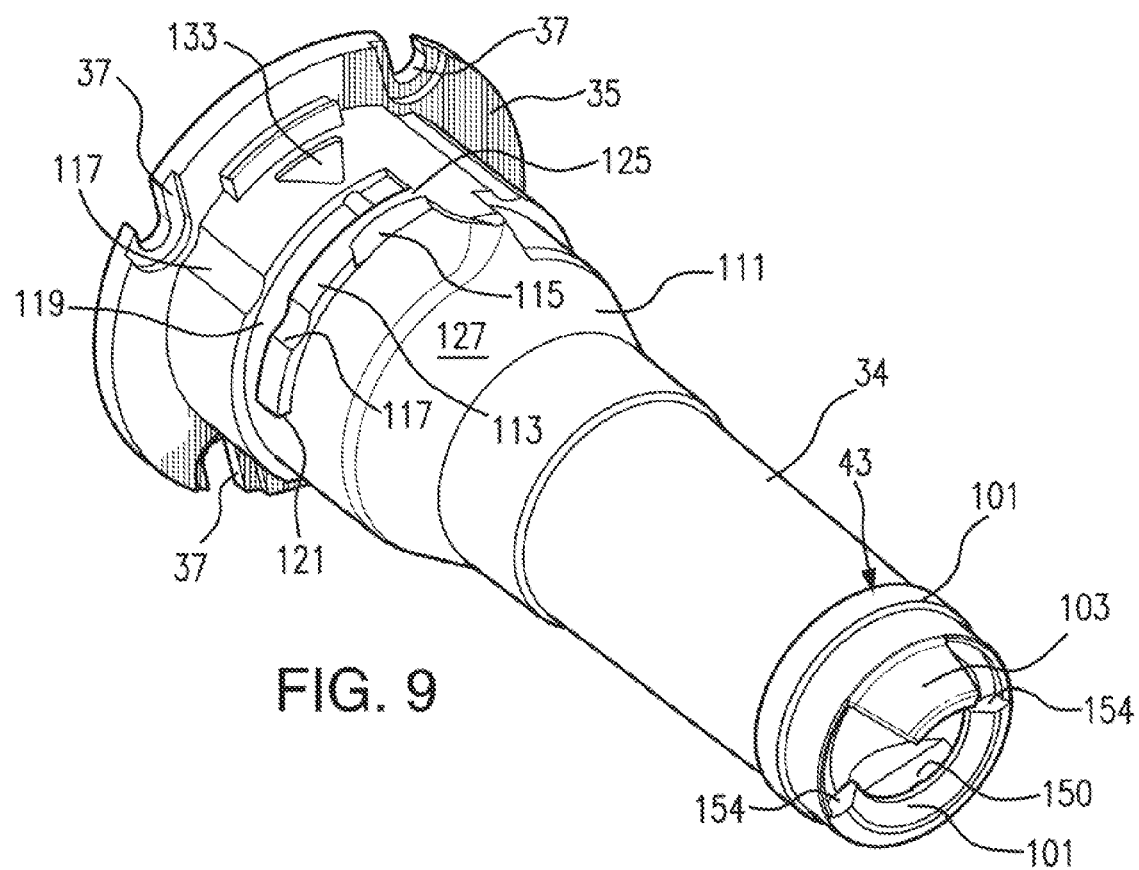
FIG. 9 is a perspective view showing the handle sleeve.

The tip sleeve 62, see FIG. 8, consists of a tube having at its forward end a ridge 65 and behind it a groove 67. At its rear end, tip sleeve 62 increases in diameter conically and terminates in a flange 69. Adjacent its rear end, a rectangular through opening 71 is formed in the shell of the tip sleeve 62. On the forward side of the opening 71 the inside of the tip sleeve 62 is thickened at 73 to form a flat shelf 75 generally the circumferential width of the opening 71. On the rear side of the opening 71 the inside of the tip sleeve is thickened to form an inwardly extending plate 77 also generally the circumferential width of the opening 71. Plate 77 has a v-notch 79 formed at its inmost extent. Reinforcing ribs 78 is on the exterior of the tip sleeve 62 extending from the conical section to the flange 69.

Figure 7:
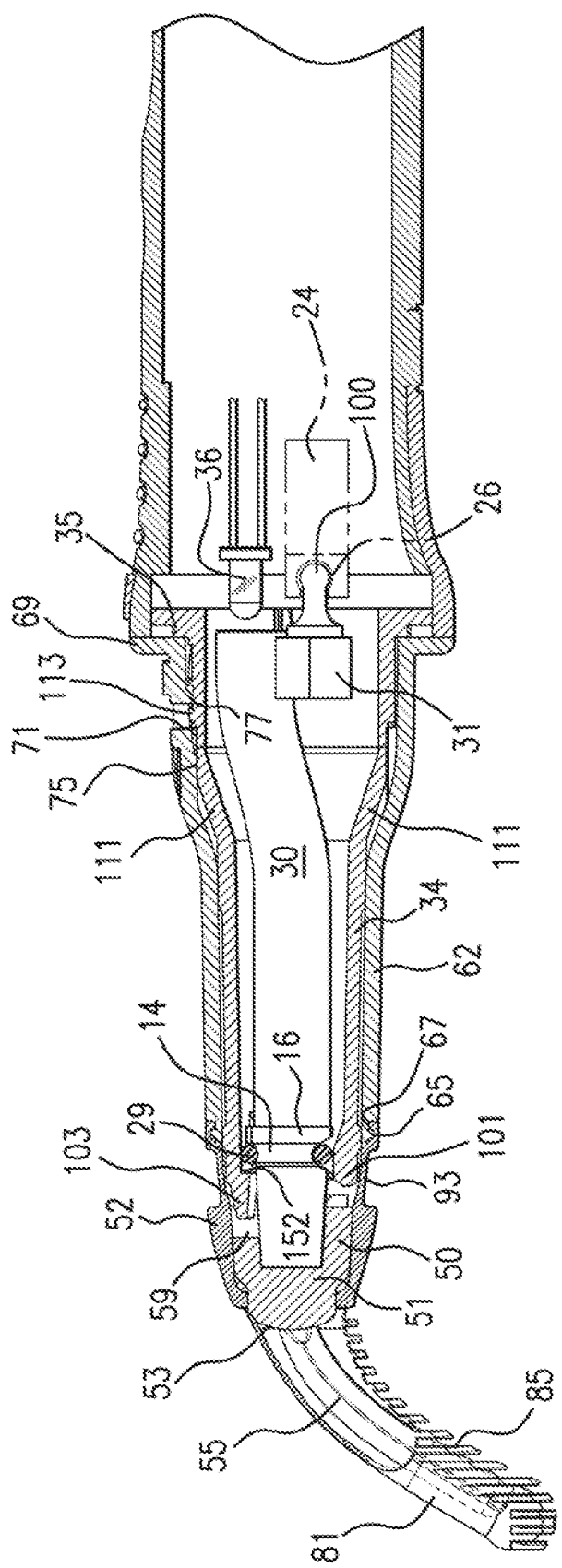
FIG. 7 is an assembly view in section of the disposable tip mounted on the handle sleeve of the instrument.

The overmold 52 is hollow and the forward portion has two longitudinally extending arms 81 that fit over the longitudinally extending legs 55. The free ends of the arms terminate in an enlarged end bulbous portion 82. The overmold 52 is composed of rubber or a thermoplastic elastomer having a durometer of preferably about 40 A but may vary from about 30 A to about 50 A. Portion 91 of the overmold fits over the cup 51 and has a hole 83 that fits around the lens 53 to let the light shine through. The two arms 81 have a series of transversely extending, longitudinally spaced grooves 85 on the underside, defined by projecting filaments, to trap saliva so reuse of the disposable tip will not be attempted. The two arms 81 of the overmold 52 can be smooth or have many filaments in the form of ribs as shown in FIG. 7, or an array of projecting filaments of any shape, projecting off of the surface of the overmold arms 81, providing a greater stimulation to the tissue while in use. An intermediate portion 87 is enlarged transversely on both arms 81 of the overmold 52 to collectively form a retractor surface 89 to help press away or retract tissue. Rear portion 92 of the overmold 52 has a reduced thinned section 93 that at the rear is integral with a terminal section 95 complementary in configuration to the forward end of the tip sleeve 62 to fit over the ridge 65 and behind it in the groove 67 to anchor the overmold 52 to the tip sleeve 62 and holds it spaced from the tip 50.

The handle sleeve 34, as shown in FIGS. 1, 2, 4, 5, 7, 9 and 10-12, is a longitudinally extending tube and has at its forward end, a circumferential radially inward flange 101 that terminates spaced from either side of a tapered protrusion or tooth 103 extending axially or longitudinally forward level with the forward end of the sleeve 34, to define recesses 154, see particularly FIGS. 10-12. The tooth 103 extends slightly into the sleeve 34 forming a rear shoulder 152. Circumferential flange 101 formed at the forward end of the handle sleeve 34 serves as a constraint on the forward side to hold the O-ring 29. O-Ring 29 also passes behind and bears on shoulder 152 of tooth 103 and thus, is constrained on the forward side also by the tooth 103. These elements together hold the light rod 30 on the forward side in position within the forward end of handle sleeve 34. On the rear side, projection 16 on the light rod is constrained by arcuate radially inwardly projections 150 one of which is seen in FIGS. 10 to 12. Also seen in FIGS. 10 to 12 are recesses 154 formed on either side of the tooth 103 between the terminating ends of the circumferential flange 101 and the tooth 103. Recesses 154 are about 1-2 mm deep. As noted, only the O-ring 29 engages the inner surrounding surface of handle tip 34. The rod 30 with the O-ring 29 acting as a pivot is otherwise completely free to vibrate.

The handle sleeve 34 at its rear end is of larger diameter with a transition conical section 111 between the front end and rear end. The rear end terminates in flange 35 having bolt opening 37. Spaced forward of the flange 35 is a surface portion 127 of the conical section 111 that is of fixed diameter. An arcuate ridge 113 is formed that extends circumferentially from a point 125 of larger diameter than portion 127 circumferentially for about 60 to 90 degrees and terminates at point 121. Ridge 113 is narrowed by cutout 115 on its right side as viewed in FIG. 9 and has a dip 117 to enable a bolt to pass through to a bolt opening 37. The ridge 113 defines a groove 119 on its rear side, due to surface 127 having a fixed diameter and a low rib 123 extends longitudinally in groove 119 to the rear of cutout 115.

Each of tip sleeve 62, handle sleeve 34 and handle 12 have indicia to show how the parts line up. Handle 12 has an arrowhead 131 pointing forward on its front end aligned with the control button 132 to turn the power on and off. Handle sleeve 34 has an arrowhead 133 pointing forward just behind the flange 35. The disposable tip 40 has an arrowhead 135 on tip sleeve 62 pointing rearward so that when the disposable tip 40 is pushed longitudinally onto the handle sleeve, the tooth 103 will be inserted or protrude into the cutout 59 of the plastic tip 50, but with clearance from both the plastic tip 50 and light rod 30 so that vibration of tip 50 by light rod 30 is not interfered with in any way. Also, the rear ends of positive ribs 61 will be received and positioned in recesses 154 in the handle sleeve 34, but with clearance from the handle sleeve 34 and tooth 103 so that tip 50 vibration is not interfered with in any way. The positive ribs 61 of tip 50 and recesses 154 of handle sleeve 34 are complementary and the clearance between them is at least about 0.5 mm. See particularly FIGS. 10-12.

As the disposable tip 40 is being pushed onto the handle sleeve 34 in a linear longitudinal direction, the thickened area at 73 that forms a flat shelf 75 causes the inwardly extending plate 77 to ride over the ridge 113 at cutout 115 and go behind into the groove 119, whereupon the flat shelf 75 drops down onto the surface 127, the rectangular through opening 71 straddles the ridge 113 at the cutout 115 and the plate 77 drops onto the rib 123 with the v-notch 93 engaging the rib 123. At this point, the rod 30 is received in and positioned in the cup 51 of the tip 50 of the disposable tip 40, which is latched onto the handle sleeve 34 and cannot be pulled off axially. The tooth 103 at the forward end of handle sleeve 34 is received in and positioned in the cutout 59 with suitable clearance all-around of at least about 0.5 mm so that there is not any interference respecting vibration. Also, the rear ends of the positive ribs 61 on either side of the cutout 59 are received in the recesses 154 to a sufficient depth to enable back-up engagement with the handle sleeve 34 in the event there is any relative rotary motion with respect to the handle sleeve 34 and the tip 50. Both the tooth 103 and the rear ends of the positive ribs 61 serve to hold the handle sleeve 34 and the tip 50 from relatively rotating. The tooth 103 and the positive ribs 61 will, at this time, be juxtaposed in the same radial cylinder coaxial with the longitudinal axis of the instrument, the handle sleeve 34 and the cutout and the tabs 61 of cup 50.

To remove the disposable tip 40 from the handle sleeve 34, it is necessary for the tip sleeve 62 to be rotated relative to the handle sleeve 34 from adjacent point 125 toward the terminal point 121 until the plate 77 clears this point 121, at which time, the disposable tip 40 can be removed by longitudinally pulling forward. However, during the relative rotary motion between the tip sleeve 62 and handle sleeve 34, the plastic tip 50 will quickly engage the tooth 103, either by the side walls of the cutout 59 or the tabs or positive ribs 61 or both and the tip 50 will then be held stationary and prevented from rotating. The tip sleeve 62 will still be rotatable relative to the handle sleeve 34 so it can be removed, and in this process as the tip sleeve 62 is rotated, a torsion force will develop and be imparted to the overmold 52 and the elastic limit of the overmold 52 at the thinned section 93 will quickly be exceeded and the overmold will experience a severe tearing or shredding of the thinned section 93 of overmold 52 over about 60 to 90 degrees or more destroying effectively its utility and/or its ability to be reused. The rear end of the positive ribs 61 of tip 50 being in the recesses 154 is a back-up in case of any failure of the tooth 103 to hold the tip 50 stationary during demounting of the disposable tip 40 from the sleeve 34. The rear ends of the positive ribs 61 being positioned in recesses 154 will also prevent any rotation of tip 50 relative to handle sleeve 34 during the demounting of disposable tip 40 and thereby insure the tearing or shredding of the thinned section 93 of overmold 52.

As described, the fitting member 31 attached to the end of the light rod 30 includes a projecting stub with ball end 100 as a cam follower for contacting and following the cam 26 to impart the vibratory motion of the cam 26 to the light rod 30. The end of the light rod 30 is in alignment with the LED 36 as previously described. Although continuous pulsing can be used, it has been discovered that a pulsed vibration sequence is more effective. A pulsed sequence of about one second on and then about a tenth of a second off, is sufficient to pulse the vibration without allowing the vibration of the tip to ever drop down to zero. In this manner, the device or instrument pulses about every second, re-stimulating the nerves in the area, and apparently the brain never gets used to it, so the vibrations remain effective. To this end the electronics controlling the pulsing is modified to include the necessary means for pulsing and obtaining the desired on/off duty cycle as noted. The motor is energized using 110 volt AC (50-300 Hz frequency). The frequency can vary from about 50 Hz to about 300 Hz with about 140 Hz to 160 Hz being preferred. The vibration at the free ends of the prongs or forks 42 can vary from about 0.1 mm to about 1.0 mm with the preferred range being 0.65 mm to 1.0 mm. The duty cycle is about 1.05 seconds with on pulsing of about 1 sec. and off of about 0.05 sec. The vibration amplitude may vary from about 0.1 mm to about 1.0 mm, with the preferred range being from about 0.65 mm to about 1.0 mm.

The novel instrument exhibits enhanced amplitude and percusses the tissue contacted, causing a deeper penetration of the vibratory stimulus into the oral mucosa of a dental patient, or into the skin of a medical patient, thereby stimulating the sensory nerve receptors, which are located deep within the tissue, creating action potentials which send sensory information to the brain via myelinated A-beta afferent nerve fiber axons.

Also, vibration is sent out in a full 360 degrees around the disposable tip 40, mainly, from three places off of the tip, namely, from each free end of the curved downwardly arms, as well as, from the paddle or retractor portion 87. Also the joint with tip sleeve 62 at times will stimulate the lip or cheek or bone when resting against it. The enhanced vibration is not limited to just the area at the ends of the curved downward arms. Alternative tip free end shapes are shown in WO/2010/111611, incorporated herein by reference.

As previously described in WO/2010/111611 a plastic sleeve or wrapper can be placed around the instrument to protect its sterility and avoid contamination during use. The plastic sleeve or wrapper has a hole punched in it so it can fit over the handle sleeve 34, and the disposable tip 40 can be mounted over the handle sleeve 34 as described. To this end, the flange at the rear of the disposable tip 40 is spaced slightly from the face of the instrument to provide a slot to accommodate the plastic sleeve or wrapper in between the instrument and the tip.

If the device or instrument is to be used for a medical application, that is, to some part of the body other than the mouth, the disposable tip 40 will curve upwardly, 180 degrees opposite from the dental application described above, and the legs of the tip member 50, or other tip member shape, can be coated or uncoated by the overmold with the overmold 260 bridging and holding together the cup of the tip member and the ribbed end of the tip sleeve 62.

It should be apparent to one skilled in the art, from the above description that the present invention can be utilized in a variety of procedures requiring a skin or flesh puncture. Such other procedures include such things as inoculations, shots to give patients medication, etc. Such skin punctures procedures can be performed on any portion of the body such as the arm, legs, buttocks, torso, etc.

The method of the invention consists in vibrating tissue of a human or animal in proximity to a preselected injection site on the human or animal body while simultaneously injecting by a needle or like instrument a liquid at the preselected injection site. The vibration is most effective if transmitted to a cylindrical volume of tissue and underlying bone at the injection site, and particularly on opposite sides of or surrounding the injection site. Also, it is preferred that a noise generator be mounted in the main body of the instrument so that the vibration is accompanied by noise that will provide a distraction. In the most preferred embodiment of the method, a pulsed vibration sequence is used. A pulsed sequence of one second on and then a 0.05 of a second off, was sufficient to pulse the vibration without allowing the vibration of the tip to ever drop down to zero. In this manner, the device or instrument pulses every second, re-stimulating the nerves in the area, and apparently the brain never gets used to it, so the vibrations remain effective.

The tip is vibrated and has a free end characterized by a shape to induce vibrations in the tissue and underlying bone, whereby the free end can be placed in proximity to a preselected injection site on a human or animal and the tissue and underlying bone at said preselected injection site is vibrated while an injection is given. The vibrations are continued even after the injection has been completed to massage the tissue to dissipate the injected liquid into the tissue and prevent tissue distension and swelling of the tissue, which is a source of pain.

Preferably, the subsequent vibration is effected with more pressure on the tissue by the person injecting to effect better massaging. The subsequent vibration can be more effective in certain areas of the mouth if the pressure applied is sufficient to sound bone beneath the tissue. An ordinarily skilled-in-the-art dentist can sense when he is applying pressure to tissue, such as the gums, and his instrument is effectively touching and in good contact or hitting on underlying bone. When such bone contact is sensed, the pressure is maintained for at least 1 up to about 90 seconds or until any tissue distension is no longer observed.

While the present invention has been shown and described herein in what are conceived to be the most practical and preferred embodiments, it is recognized that departures, modifications, adaptations and variations may be made therefrom without departing from the intended scope of the invention as set forth in the appended claims.

What is claimed is:

1. A method for reducing pain associated with a skin-puncturing procedure of tissue of a human or an animal, the method comprising: providing an instrument having:
   (a) a main body having a forward end;
   (b) a lightpipe projecting from the forward end of the main body;
   (c) a single-use tip having a tip sleeve removably mounted on the forward end of the main body and a tip member removably mounted on the lightpipe; and
   (d) an elastic overmold covering the tip sleeve and the tip member;
   selecting a puncture site on the tissue; creating vibrations in the main body; transmitting the vibrations through the lightpipe to the tip member to vibrate the tip member;
   applying the tip member to the tissue at the puncture site, while the vibrations are transmitted through the lightpipe to the tip member, whereby the tissue is vibrated at the puncture site;
   puncturing the tissue with a needle at the tissue puncture site, wherein vibrating the tissue facilitates pain reduction during the puncturing; and
   upon completion, tearing the elastic overmold from the tip such that the tip cannot be reused.

2. The method according to claim 1, wherein tearing the elastic overmold includes rotating the tip sleeve while the tip member remains stationary.

3. The method according to claim 1, further comprising illuminating the injection site by activating the lightpipe.

4. The method according to claim 1, wherein creating the vibrations includes creating continuous vibration.

5. The method according to claim 1, wherein creating the vibrations includes creating pulsed vibrations.

6. The method according to claim 5, further comprising creating pulsed vibrations according to a pulsing duty cycle of 1.05 seconds with about one second on and about 0.05 seconds off.

7. The method according to claim 1, wherein creating the vibrations includes creating vibrations in an amplitude of about 0.1 mm to about 1.0 mm.

8. The method according to claim 1, further comprising continuing vibration of the tissue at the puncture site after the puncturing is complete.

9. The method according to claim 8, further comprising applying increased pressure to the tissue.

10. The method according to claim 9, further comprising contacting bone underlying the tissue with the increase pressure.

11. The method according to claim 10, further comprising maintaining pressure for at least 1 and up to about 90 seconds after the bone is contacted.

\* \* \* \* \*